US006410588B1

(12) United States Patent
Feldmann et al.

(10) Patent No.: US 6,410,588 B1
(45) Date of Patent: Jun. 25, 2002

(54) USE OF CANNABINOIDS AS ANTI-INFLAMMATORY AGENTS

(75) Inventors: Marc Feldmann, London; Anne-Marie Malfait, Surrey, both of (GB); Ruth Gallily; Raphael Mechoulam, both of Jerusalem (IL)

(73) Assignees: The Mathilda and Terence Kennedy Institute of Rheumatology, London (GB); Yissum Research and Development Company of the Hebrew University of Jerusalem, Jerulasem (IL)

( * ) Notice: Subject to any disclaimer, the term of this patent is extended or adjusted under 35 U.S.C. 154(b) by 0 days.

(21) Appl. No.: 09/673,207

(22) PCT Filed: Apr. 14, 1999

(86) PCT No.: PCT/GB99/01140

§ 371 (c)(1),
(2), (4) Date: Mar. 6, 2001

(87) PCT Pub. No.: WO99/52524

PCT Pub. Date: Oct. 21, 1999

(30) Foreign Application Priority Data

Apr. 14, 1998 (GB) ............................................ 9807639

(51) Int. Cl.[7] ............................................... A61K 31/35

(52) U.S. Cl. ...................... 514/454; 514/456; 514/719
(58) Field of Search .................... 549/390; 568/747, 568/766; 514/454, 456, 719

(56) References Cited

U.S. PATENT DOCUMENTS

| 4,973,603 A | 11/1990 | Burstein ..................... 514/454 |
| 5,521,215 A | 5/1996 | Mechoulam et al. ....... 514/454 |

FOREIGN PATENT DOCUMENTS

| DE | 2700340 A | 7/1977 |
| WO | 9401429 A1 | 1/1994 |

OTHER PUBLICATIONS

Holdcroft, A.; Smith, M.; Smith, B.; Hodgso, 'Clinical trial experience with cannabinoids' CA 128:110760 (1997).*
Formukong, E. A., 'Analgesic and anti–inflammatory activity of constituents of *Cannabis sativa* L' CA 109:122008 (1988).*
M. L. Barrett et al., Experientia, 42, 1986, pp. 452–453.
M. L. Barrett et al., Biochemical Pharmacology, vol. 34, No. 11, 1985, pp. 2019–2024.
E. A. Formukong et al, Phytotherapy Research, vol. 3, No. 6, 1989, pp. 219–231.
Louis Lemberger, Annual Review of Pharmacology & Toxicology, vol. 20, 1980, pp. 151–172.
Fred J. Evans, Pharmaceutical Sciences, vol. 3, 1997, pp. 533–537.
Christine Gray, Pharmaceutical Journal, vol. 254, 1995, pp. 771–773.
E. A. Formukong et al., Phytotherapy Research, vol. 5, 1991, pp. 258–261.
A. T. Evans et al., Biochemical Pharmacology, vol. 36, No. 12, 1987, pp. 2035–2037.
A. T. Evans et al., 122nd British Pharmaceutical Conference, Sep. 9–12, 1985, Journal of Pharmacy and Pharmacology, vol. 37, 1985, p. 43P.
Journal of Pharmacy Technology, vol. 12, Nov./Dec. 1996, p. 294.
Ladislav Volicer, American Family Physician, vol. 55, 1997, p. 1338.
W. D. Lyman et al., Journal of Neuroimmunology, vol. 23, 1989, pp. 73–81.
W. D. Lyman, Advances in Experimental Medicine and Biology, vol. 288, 1991, pp. 81–92.
R. Elkin et al., Fed. Proc. Experimental Biology, vol. 46, 1987, p. 1378.
C.N. Martyn et al., Lancet, vol. 345, Mar. 4, 1995, p. 579.
Itzhak Wirguin et al., Immunopharmacology, vol. 28, 1994, pp. 209–214.
J. Thornas Ungerleider et al., Advances in Alcohol and Substance Abuse, vol. 7, 1987, pp. 39–50.
William A. Check, JAMA, vol. 241, 1979, p. 2476.
David B. Clifford, Ann. Neurol., vol. 13, 1983, pp. 669–671.
Donald P. Tashkin, Biochemistry and Physiology of Substance Abuse, vol. 3, 1991, pp. 41–70.
B.J. Shapiro et al., Chest, vol. 71, 1977, pp. 558–560.
S.J. Williams et al., Thorax, vol. 31, 1976, pp. 720–723.
Donald P. Tashkin et al., American Review of Respiratory Disease, vol. 109, 1974, pp. 420–428.
D.P. Tashkin et al., Am. Rev. Respir. Diseases, vol. 119, 1979, p. 82.
J.P.R. Hartley et al., Br. J. Clin. Pharmacol., vol. 5, 1978, pp. 523–525.
Bernhard Watzl et al., Int. J. Immuno. Pharmac., vol. 13, 1991, pp. 1091–1097.
Raphael Mechoulam, Marijuna Chemistry, Metabolism and Clinical Effects, Academic Press, New York, 1973, pp. 1–99.
Leo E. Hollister, Pharmacological Reviews, vol. 38, No. 1, 1986, pp. 1–20.
William L. Dewey, Pharmacological Reviews, vol. 38, No. 2, 1986, pp. 151–177.

(List continued on next page.)

*Primary Examiner*—Amelia Owens
(74) *Attorney, Agent, or Firm*—Birch, Stewart, Kolasch & Birch, LLP

(57) ABSTRACT

The application relates to the identification that cannabinoids, such as cannabidiol can be used to treat inflammatory diseases. Cannabinoids for use in treating inflammatory diseases, methods of treating inflammatory diseases and cannabinoids in combination with pharmaceutically acceptable carriers are claimed.

7 Claims, 12 Drawing Sheets

OTHER PUBLICATIONS

D.R. Compton et al., Pharmacological Aspects of Drug Dependence: Toward an Integrated Neurobehavioral Approach, Handbook of Experimental Pharmacology, vol. 118, 1996, pp. 83–158.

A. Jacob et al., J. Chem. Soc., 1940, pp. 649–653.

Roger Adams et al., J. Amer. Chem. Soc., vol. 62, 1940, pp. 2194–2196.

R. Mechoulam et al., Tetrahedron, vol. 19, 1963, pp. 2073–2078.

Raphael Mechoulam, Tetrahedron Letters, No. 12, 1967, pp. 1109–1111.

Arthur C. Cope et al., J. Amer. Chem. Soc., vol. 87, pp. 3273–3275.

T. Petrzilka et al., Helvetica Chimica Acta, vol. 50, No. 73–74, 1967, pp. 719–723.

Science, vol. 169, Aug. 1970, pp. 611–612.

L. Murphy et al, Marijuana/Cannabinoids, CRC Press, Boca Raton, 1992, pp. 1–33.

J. Roberto Leite et al., Pharmacology, vol. 24, 1982, pp. 141–146.

J. Clin. Psychiatry, vol. 56, Oct. 1995, pp. 485–486.

Margaret S. Smith et al., Proc. Soc. Exp. Bio. Med., vol. 214, 1997, pp. 69–75.

E.A. Formukong et al., Inflammation, vol. 12, No. 4, 1988, pp. 361–371.

Ronald G. Coffey et al., Biochemical Pharmacology, vol. 52, 1996, pp. 743–751.

Bernhard Watzl et al., Adv. Esp. Med. Biol., vol. 288, 1991, pp. 63–70.

A.W. Zuardi et al., Psychopharmacology, vol. 104, 1991, pp. 260–264.

* cited by examiner

USE OF CANNABINOIDS AS ANTI-INFLAMMATORY AGENTS

This application is the national phase under 35 U.S.C. §371 of PCT International Application No. PCT/GB99/01140 which has an International filing date of Apr. 14, 1999, which designated the United States of America.

BACKGROUND OF THE INVENTION

1. Field of Invention

This application relates to anti-inflammatory agents, and in particular to the use of cannabinoids for the treatment of inflammatory diseases such as rheumatoid arthritis, multiple sclerosis and Crohn's Disease, and to medicinal preparations containing cannabinoids.

2. Background Art

*Cannabis sativa*, commonly known as marijuana, has been used for several years for its medicinal effects, including antipyretic and analgesic properties. Approximately 80 cannabis constituents, termed cannabinoids, naturally occur as 21 carbon atom compounds of cannabis and analogues of such compounds and their metabolites [Mechoulam, In "Marijuna Chemistry, Metabolism and Clinical effects, Academic Press, New York (1973), pages 1–99].

The major psychoactive component of marijuana is Delta-9-tetrahydrocannabinoid (THC), which has been widely studied. Studies have shown that THC affects growth, development and reproductive activity [Pharmacol Rev. 38 (1986), pages 1–18 and 151–178; Marihuana, Pharmacological Aspects of Drug Dependence, Springer Verlag (1996), pages 83–158]. Studies in mice have shown that THC suppresses antibody formation against sheep red blood cells and causes changes in cytokine production. In vitro studies, however, have shown that THC may suppress or enhance (depending on dosage) the production of various cytokines such as IL-1, IL-6 and TNFα by leukocytic cells.

Cannabidiol (CBD) is present in most cannabis preparations (hashish, marijuana, ganja) in higher concentrations than THC. Cannabidiol. was, first isolated in 1940 by Todd and Adams [J. Amer. Chem. Soc., 6,2 2194 (1940), J. Chem. Soc., 649 (1940)]. Its structure was elucidated by Mechoulam and Shvo in 1963 [Tetrahedron, 19 (1963), page 2073]. Its absolute stereochemistry was determined in 1967 [Tet. Lett., 1109–1111 (1967)]. The synthesis of cannabidiol in its racemic form and its natural form were reported in the 1960's [J. Amer. Chem. Soc., 87, 3273–3275 (1965), Helv. Chim. Acta, 50 719–723 (1967)].

Cannabidiol has no psychotropic (cannabimimetic activity) and does not bind either the brain or the peripheral receptors, CB1 and CB2 respectively [Science 169, 611–612 (1970); "Marijuana/cannabinoids: neurobiology and neurophysiology", ed. L. Murphy and A. Bartke, CRC Press, Boca Raton, 1–33 (1992)]. Cannabidiol has, however, been observed to have anticonvulsant effects [Pharmacol, 124, 141–146 (1982)]. Cannabidiol has also been effective in animal models predictive of antipsychotic activity, and has been found to have antipsychotic effects in the case of schizophrenia [Psychopharmacol., 104, 260–264 (1991); J. Clin. Psychiatry, 56 485–486 (1995)].

Cannabidiol has sporadically been studied for its immunomodulatory effects in vivo and in vitro. Smith et al [Proc. Soc. Exp. Bio Med. 214 (1997), pages 69–75] demonstrated that BALB/C mice injected with cannabidiol did not show significant change in the level of mRNA of IL-1, IL-6 and TNFα. At an 8 mg/kg dose of cannabidiol, the mortality of mice sublethally injected with Legionella was not affected.

Preliminary studies by Formukong et al [Inflammation, 12, 361–371 (1988)] showed that cannabidiol inhibited PBQ-induced writhing in mice when given orally at doses up to 10 mg/kg. Cannabidiol was also shown to reduce TPA-induced erythema, which is dependent upon prostaglandin release, in mice when applied topically.

In an in vitro study, Coffey et al [Biochem. Pharmacol, 52 (1996), pages 743–51] demonstrated that THC and cannabidiol inhibited nitric oxide (NO) produced by mouse peritoneal macrophages activated by LPS and IFNγ. Watzl et al [Drugs of Abuse, Immunity and Immunodeficiency, Plenum Press, New York, .63–70 (1991)] studies in vitro the effects of THC and cannabidiol on secretions of IL-1, IL-2, IL-6, TNFα and IFNγ by human leukocytes following activation by mitrogen, They found that both cannabinoids in low concentrations increase IFNγ production, whereas in high concentrations (5–24 μg/ml) completely blocked IFNγ synthesis, and cannabidiol decreased both IL-1 and TNFα production and did not affect IL-2 secretion.

SUMMARY OF THE INVENTION

The inventors have now unexpectedly found that cannabinoids may be used to treat inflammatory diseases, such as rheumatoid arthritis and Crohn's disease. Inflammatory diseases involve the complex interaction between several components such as Interleukins (IL-1, IL-6 and IL-8), TNF-α and various mediators such as nitric oxide, ROI and $PGE_2$.

Cannabinoids have been found by the inventors to act as anti-inflammatory agents in vivo.

Accordingly, a first aspect of the invention provides use of one or more cannabinoids as an anti-inflammatory agent.

Preferably, the cannabinoid is an isolated cannabinoid such as cannflavone-2 (formula I) or a cannabinoid having the general formula II.

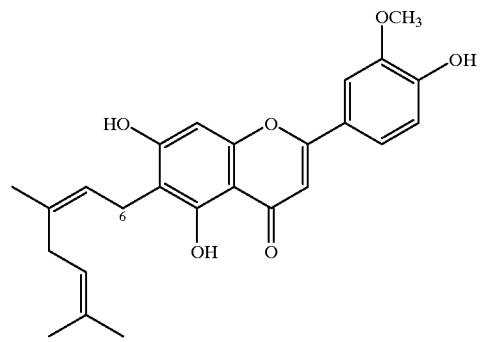

Formula I

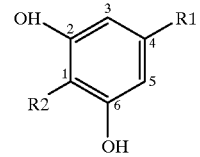

Formula II where:
  R1 is a straight or branched chain saturated or unsaturated alkyl having preferably 2 to 6 carbon atoms, especially 5 carbon atoms;
  R2 is H or a saturated or unsaturated straight, branched or cyclic hydrocarbon group, or forms a substituted or unsubstituted cyclic ether with the O atom at the sixth position.

Especially preferred cannabinoids are:

Formula III

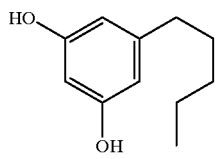

olivetol

Formula IV

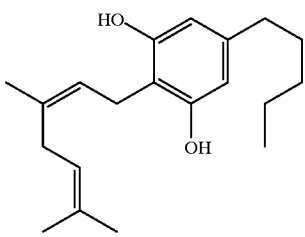

cannabigerol

Formula V

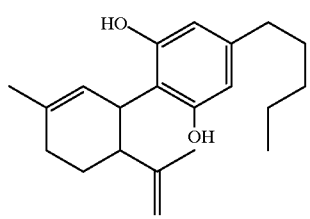

cannabidiol

Formula VI

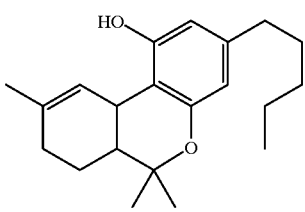

tetrahydrocannabinol

Formula VII

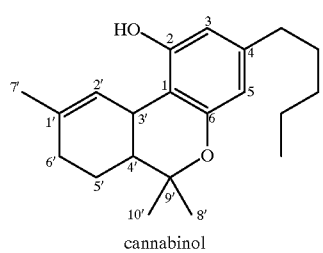

cannabinol

The term isolated is intended to include a naturally occurring cannabinoid which has been purified from a natural source or one which has been chemically synthesised.

Preferably the cannabinoid is used as an anti-inflammatory agent against inflammatory diseases, especially rheumatoid arthritis or Crohn's Disease, sarcoidosis, asthma, Alzheimer s disease, multiple sclerosis, Psoriasis, ulcerative colitis, osteoarthritis or spondyloarthropathy (erg. ankylosing spondylitis).

The invention also provides a method of treating a patient suffering from an inflammatory disease comprising the step of administering to the patient a pharmaceutically acceptable amount of a cannabinoid.

The cannabinoid is preferably as defined above.

The patient is preferably a mammal such as a human.

Cannabinoids may be used separately or as mixtures of two or more cannabinoids. They may be combined with one or more pharmaceutically acceptable compounds such as carriers.

The invention also provides the use of one or more cannabinoids as previously defined in the manufacture of a medicament to treat inflammatory diseases.

A further aspect of the invention provides a method of treating an inflammatory disease comprising the step of administering to a patient one or more cannabinoids as previously defined. The cannabinoids may for example be applied orally, intramuscularly, subcutaneously, intradermally, intravenously, by nasal spray or topically.

As a general proposition, the total pharmaceutically effective amount of cannabinoid administered will be in the range of 1 $\mu$g/kg/day to 50 mg/kg/day of patient body weight, preferably 2.5 to 10 mg/kg/day especially 5 mg/kg/day.

Accordingly. the invention also relates to medicinal preparations, including topical formulations, capsules, tablets and/or injectable formulations, containing one or more cannabinoids as previously defined for use as anti-inflammatory agents.

Preferably the cannabinoids, according to any previous aspect of the invention, are used or combined with one or more known anti-inflammatory compounds, especially anti-rheumatoid arthritis compounds, such as methotrexate. This allows advantageous properties of the cannabinoids to be combined with known properties of the known compound (s).

The invention will now be described by way of example only with reference to the figures in which:

DETAILED DESCRIPTION OF THE INVENTION

EXAMPLE 1

Figure 1:
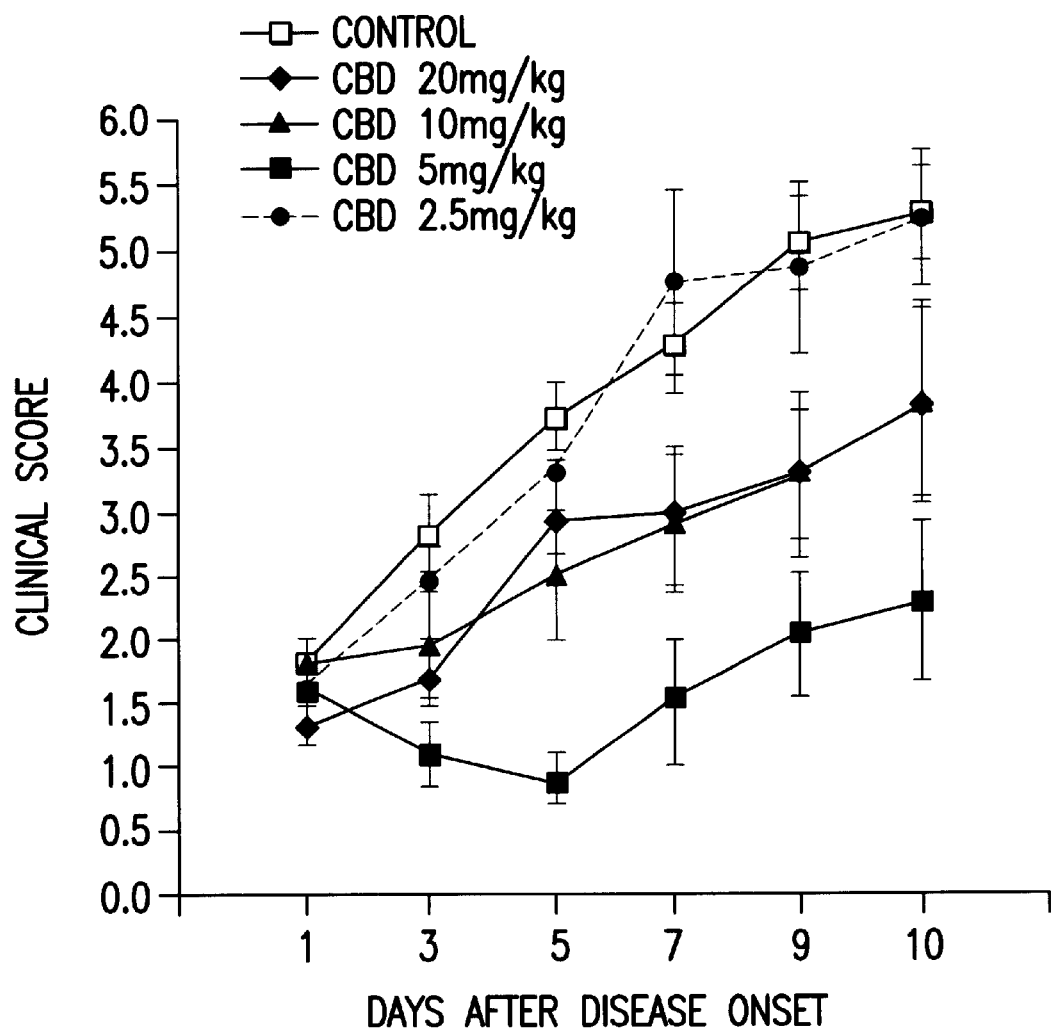
FIG. 1 shows the clinical scores for mice treated with CBD (cannabidiol). Using the Mann-Whitney U-test for comparison of non-parametric data, the following p-values were obtained when comparing treated mice with control mice: for 20 mg/kg, p<0.05 at day 3, day 7 and day 9; for 10 mg/kg. p<0.05 for days 3, 5, 7 and 9; for 5 mg/kg. p=0.004 at day 3, p=0.0096 at day 5; p=0.0269 at day. 7, and p=0.0285 at day 9.

Effect of CBD on TNFα Production by Thioalycollate-induced Macrophages

Thioglycollate-elicited peritoneal macrophages from C57BL/6 mice were activated with LPS and IFNγ. Effects of different concentrations of CBD on the production TNFα was studied. IFN-γ and IFN-α were purchased from Boehringer Mannheim, Germany. The results are shown in Table 1.

TABLE 1

Effect of CBD on TNFα production by Thioglycollate induced macrophages.

| CELLS & AGENT | 6 h | % INHIBITION | 24 h | % INHIBITION |
|---|---|---|---|---|
| A) ACTIVATION BY LPS 1 μg/ml | | | | |
| 0 | 0.4 | | 9 | |
| LPS | 596 | | 277 | |
| LPS + CBD 6 μg/ml | 290 | 51 | 34 | 88 |
| LPS + CBD 4 μg/ml | 271 | 54 | 36 | 87 |
| LPS + CBD 2 μg/ml | 543 | 9 | 90 | 67 |

TABLE 1-continued

Effect of CBD on TNFα production by Thioglycollate induced macrophages.

| CELLS & AGENT | 6 h | % INHIBITION | 24 h | % INHIBITION |
|---|---|---|---|---|
| B) ACTIVATION BY LPS 1 μg/ml + IFNγ 10 U/ml | | | | |
| 0 | 0.4 | | 9 | |
| LPS + IFNγ | 716 | | 2664 | |
| LPS + IFNγ 6 CBD μg/ml | 548 | 24 | 207 | 92 |
| LPS + IFNγ 4 CBD μg/ml | 478 | 33 | 437 | 84 |
| LPS + IFNγ 2 CBD μg/ml | 744 | 0 | 4578 | enhanced 72% |

Thioglycoiate-elicited peritoneal macrophages from C57BL/6 mice.

Table 1 shows that CBD inhibits TNFα production. Low concentrations of CBD appear to enhance TNFα production.

EXAMPLE 2

The Effects of CBD on Nitric Oxide Production was Also Studied

Results are shown in Table 2.

TABLE 2

Effect of CBD on nitric oxide (NO) generation by Thioglycollate induced macrophages.

| CELLS & AGENT | 24 h | % INHIBITION | 48 h** | % INHIBITION |
|---|---|---|---|---|
| A) ACTIVATION BY LPS (1 μg/ml) NO (nM)* | | | | |
| CONTROL | 0.1 | | 0.3 | |
| LPS 1 μg/ml | 5.4 | | 7.3 | |
| LPS 1 μg/ml + CBD 8 | 0.1 | 99 | 0.4 | 95 |
| LPS 1 μg/ml + CBD 6 | 0.1 | 99 | 2.1 | 71 |
| LPS 1 μg/ml + CBD 4 | 0.5 | 90 | 4.6 | 37 |
| LPS 1 μg/ml + CBD 2 | 3.7 | 32 | 6.7 | 9 |
| B) Activation by LPS 1 μg/ml + IFNγ 10 U/ml NO (nM)* | | | | |
| LPS + IFNγ | 13.9 | | 20.5 | |
| LPS + IFNγ + CBD 8 | 0.2 | 99 | 3.1 | 85 |
| LPS + IFNγ + CBD 6 | 5.5 | 61 | 18.1 | 11.5 |
| LPS + IFNγ + CBD 4 | 6.9 | 51 | 21.3 | -(↑ 4%) |
| LPS + IFNγ + CBD 2 | 12 | 14 | 25.4 | -(↑ 24%) |

*Assayed by Griess reagent
**After 48 hr the Mφ cultured with 8 μg/ml CBD were only 70% viable Once again, low concentrations of CBD appear to activate nitric oxide production, whilst higher concentrations inhibit nitric oxide production.

EXAMPLE 3

In Vitro Effects on Human Peripheral Blood Mononuclear Cells

Preparation of CBD for in Vitro Experiments

CBD was dissolved in ethanol/DMSO. The ethanol was subsequently evaporated by means of a SpeedVac, and the CBD was resuspended in warm medium at a stock concentration of 1 mg/ml.

Culture of Human Peripheral Blood Mononuclear Cells

Peripheral blood mononuclear cells (PBMC) were isolated from the whole blood of healthy donors by Ficoll Hypaque gradient. They were cultured at $2 \times 10^5$ cells/ml in 96-well microtitre plates (200 μ/well) and incubated for 6 hours with a dose range of CBD (from μg/ml). After this 6 hour pretreatment period, the cells were stimulated with either LPS from Salmonella typhimirium, 10 ng/ml, for 24 hours (for TNF and IL-1β) or with PHA, 5 μg/ml, for 72 hours (for IFNγ) Viability of the PBMC was assessed with the MTT test.

Results

In Vitro Effects of CBD on Cytokine Release by Cultured Cells

Figure 2:
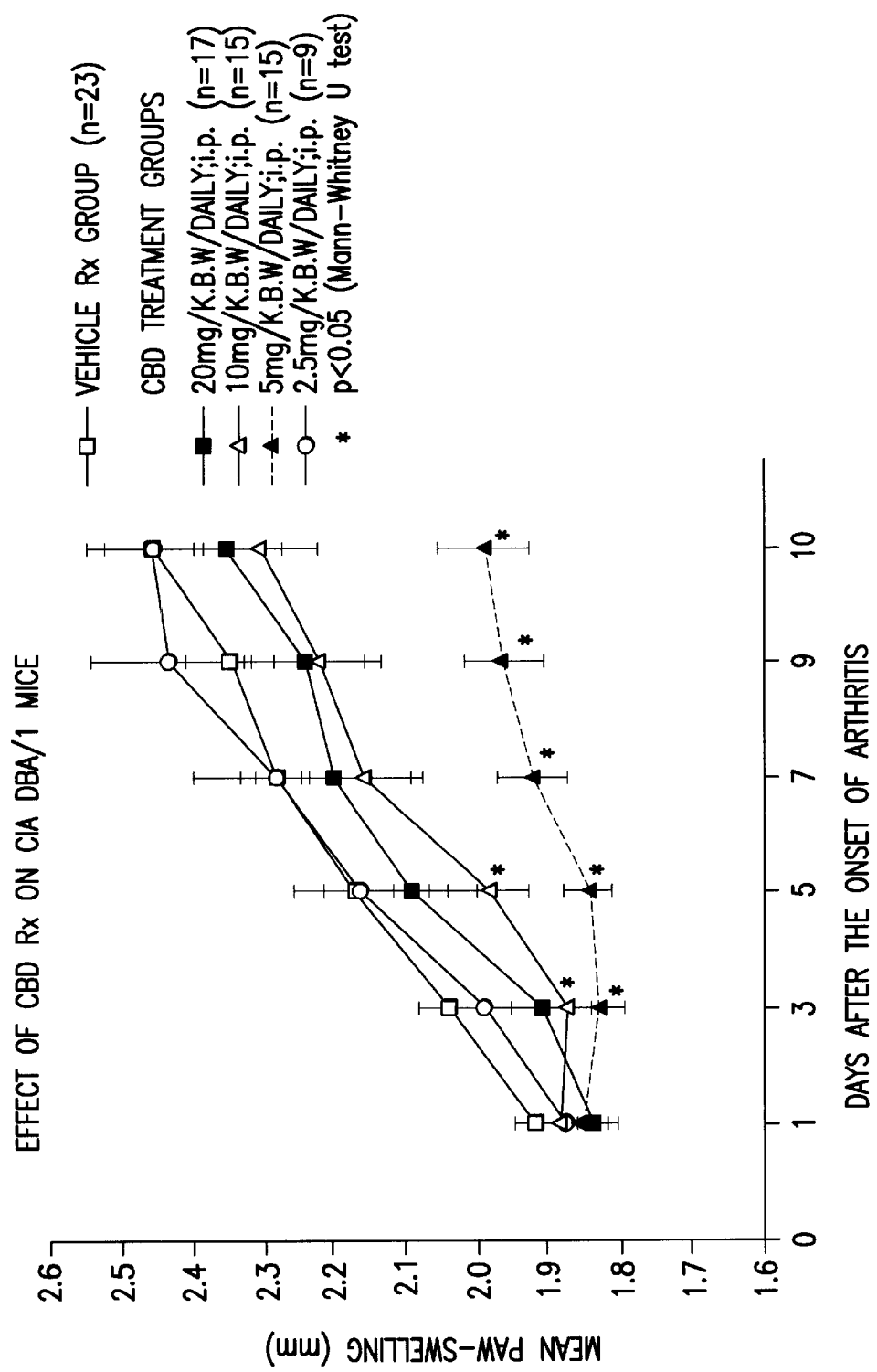
FIG. 2 shows the effect of CBD on paw thickness. For 10 mg/kg. p=0.004 at day 3 and p=0.0145 at day 5; for 5 mg/kg. p=0.0001 at day 3 and p<0.0001 at days 5, 7, 9

Table 3 summarizes the effects of CBD on activated human PBMC. Interestingly, it was found that the lower concentrations of CBD (0.1 to 5 μg/ml) significantly suppressed the release of the LPS-induced proinflammatory cytokines TNFα and IL-1β, whereas the higher concentrations increased their release. This finding was reproducible and is important in view of the fact that we also found a bell-shaped effect in vivo when treating arthritic mice with CBD. The highest dose of 20 mg/kg i.p. was not capable of ameliorating arthritis (FIGS. 1 and 2).

TABLE 3

|  | TNF α (pg/ml) | IL-1β (pg/ml) | IFNγ (pg/ml) |
|---|---|---|---|
| Cells only | 27 ± 2 | 40 ± 0 | 82 ± 12 |
| Cells + stimulus in vehicle | 8889 ± 195 | 1408 ± 165 | 1881 ± 114 |
| CBD 0.1 μg/ml | 2959 ± 434 | 621 ± 82 | 2062 ± 316 |
| CBD 1 μg/ml | 2503 ± 181 | 671 ± 74 | 1082 ± 75 |
| CBD 2.5 μg/ml | 3071 ± 296 | 630 ± 81 | 1171 ± 138 |
| CBD 5 μg/ml | 4152 ± 499 | 908 ± 99 | 791 ± 43 |
| CBD 10 μg/ml | 10,964 ± 1714 | 1575 ± 335 | 150 ± 43 |
| CBD 20 μg/ml | 15,071 ± 2594 | 2292 ± 251 | ND |
| CBD 30 μg/ml | 20,824 ± 1046 | 4158 ± 313 | ND |

Table 3

Human PBMC were cultured and stimulated with or without CBD, as described in Materials and Methods. The stimulus for TNF and IL-1 production was LPS, the stimulus for IFNγ production was PHA. The results are the mean of triplicate wells±SEM. ND=not done.

EXAMPLE 4

In Vivo Studies on the Effect of CBD

Induction and Monitoring of Collagen Induced Arthritis

Bovine type II collagen (CII) was purified from hyaline cartilage, as described [Williams, 1992# 18]. Male DBA/1 mice (8–12 weeks old) were immunized with 100 μg of CII emulsified in complete Freund's adjuvant CFA (Difco, Detroit, Mich.) by intradermal injection at the base of the tail. From day 15 after immunization onwards, mice were examined daily for onset of CIA using two clinical parameters: paw swelling and clinical score [Williams, PNAS, Vol. 89, pages 97848]. Paw swelling was assessed by measuring the thickness of the affected hind paws with 0–10 mm callipers (Kroeplin, Schluchtern, Germany). For the clinical score, 0=normal; 1=slight swelling and erythema; 2=pronounced edema; 3=joint rigidity. Each limb was graded, resulting in a maximal clinical score of 12 per animal. The arthritis was monitored over 10 days, after which the mice were sacrificed.

For the chronic experiments, 6 weeks old mice were immunized with mouse CII (100 μg CII i.d.=intradermal). From day 30 after immunization onwards, the mice developed a chronic relapsing arthritis, which was monitored for 5 weeks, in the same way as described above.

Administration of Cannabidiol

Cannabidiol (CBD) treatment commenced at the onset of disease and was administered i.p. daily until day 10 of arthritis in the acute arthritis model with bovine CII. The CBD concentrations used were 20 mg/kg (n=17), 5 mg/kg (n=15), and 2.5 mg/kg (n=9). CBD was dissolved in ethanol/cremophor (Sigma Chemical Co., Poole, UK) (1/1, v/v) and further diluted in saline. Mice injected with vehicle alone (ethanolcremophor in saline) served as controls (n=23).

For the chronic experiment with mouse CII, mice were treated from the first symptoms of arthritis every other day, for 5 weeks. For the i.p. route CBD was injected at doses of 10 mg/kg (n=7) and 5 mg/kg (n=7). Again, mice injected with Vehicle alone served as controls (n=7). For the oral route, the treatment was administered daily at a dose of 25 mg/kg (n=6) and control mice were fed olive oil (n=6).

For the oral treatment protocol in the acute CIA model, CBD was dissolved in olive oil and administered by oral gavage, daily, from the onset of arthritis for 10 days. The doses used were 10 mg/kag, 25 mg/kg and 50 mg/kg (n=6 per group), corresponding to 2, 5, and 10 mg/kg i.p. respectively. Control mice were fed olive oil (n=6).

Histological Analysis

Hind paws and knee joints were removed post mortem on the tenth day of arthritis, fixed in formalin and decalcified in 5% EDTA. Paws and knees were then embedded in paraffin, sectioned and stained with haematoxylin and eosin. Arthritic changes in the ankle, the metatarsophalangeal joints, the proximal interphalangeal and the distal interphalangeal joints were scored blindly as mild (mild synovial hyperplasia), moderate (pannus formulation and erosions limited to the cartilage-pannus junction), or severe (=extended bone and cartilage erosions with loss of joint architecture).

Results

CBD has a Dose-dependent Therapeutic Effect on CIA

CBD at the doses of both 20 mg/kg and 10 mg/kg had a slight therapeutic effect on CIA, especially on the clinical score (FIG. 1). The beneficial effect of 10 mg/kg seemed better than that of 20 mg/kg, particularly during the first few days of treatment (FIG. 1). It was therefore decided to lower the dose of CBD to 5 mg/kg. This concentration caused a dramatic suppression of ongoing CIA, as assessed by both the clinical score (FIG. 1) and the paw thickness (FIG. 2). The therapeutic action of CBD was lost by further lowering the concentration to 2.5 mg/kg (FIGS. 1 and 2). At this low dose, CBD was found to have no effect at all on the progression of clinical arthritis, as assessed by clinical score and paw thickness (FIG. 1 and FIG. 2).

Figure 4:
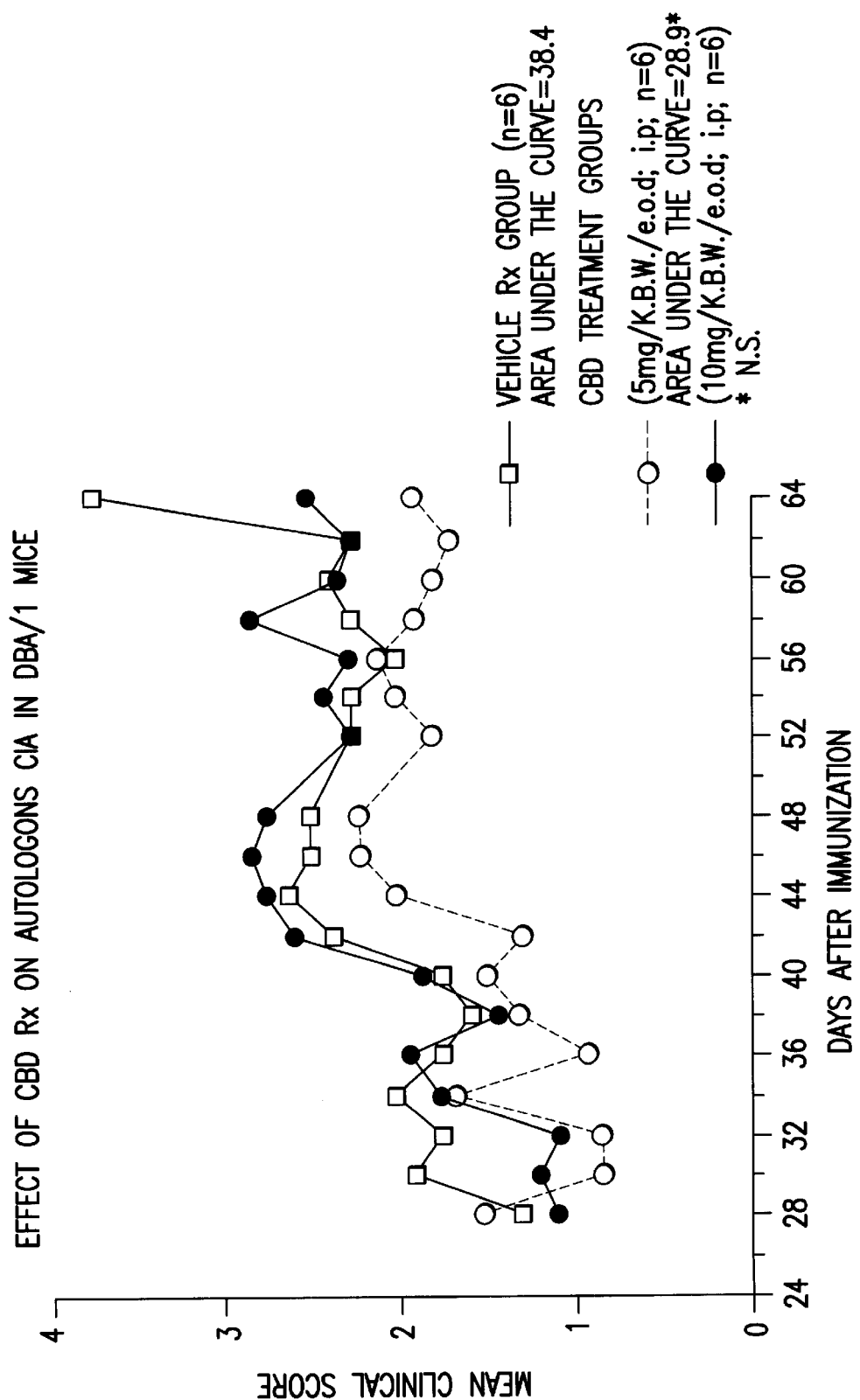
FIG. 4 shows dose-dependent effects of CBD in a chronic CIA model. From the first signs of joint swelling mice were treated 3 times a week over a 5 week period with CBD, 5 mg/kg or 10 mg/kg i.p. Control mice were treated with vehicle alone, as described in Materials and Methods. Results are expressed as a mean of 6 mice. The AUC for the control group is 38.4, and for the 5 mg/kg group 28.9.

The dose-dependent effects of CBD were confirmed in the chronic CIA model (FIG. 4). It was found that 5 mg/kg was optimal in suppressing the arthritis. The area under the curve (AUC) was 28.9, as compared to 38.4 in the control group. 10 mg/kg was less effective than 5 mg/kg.

Figure 5:
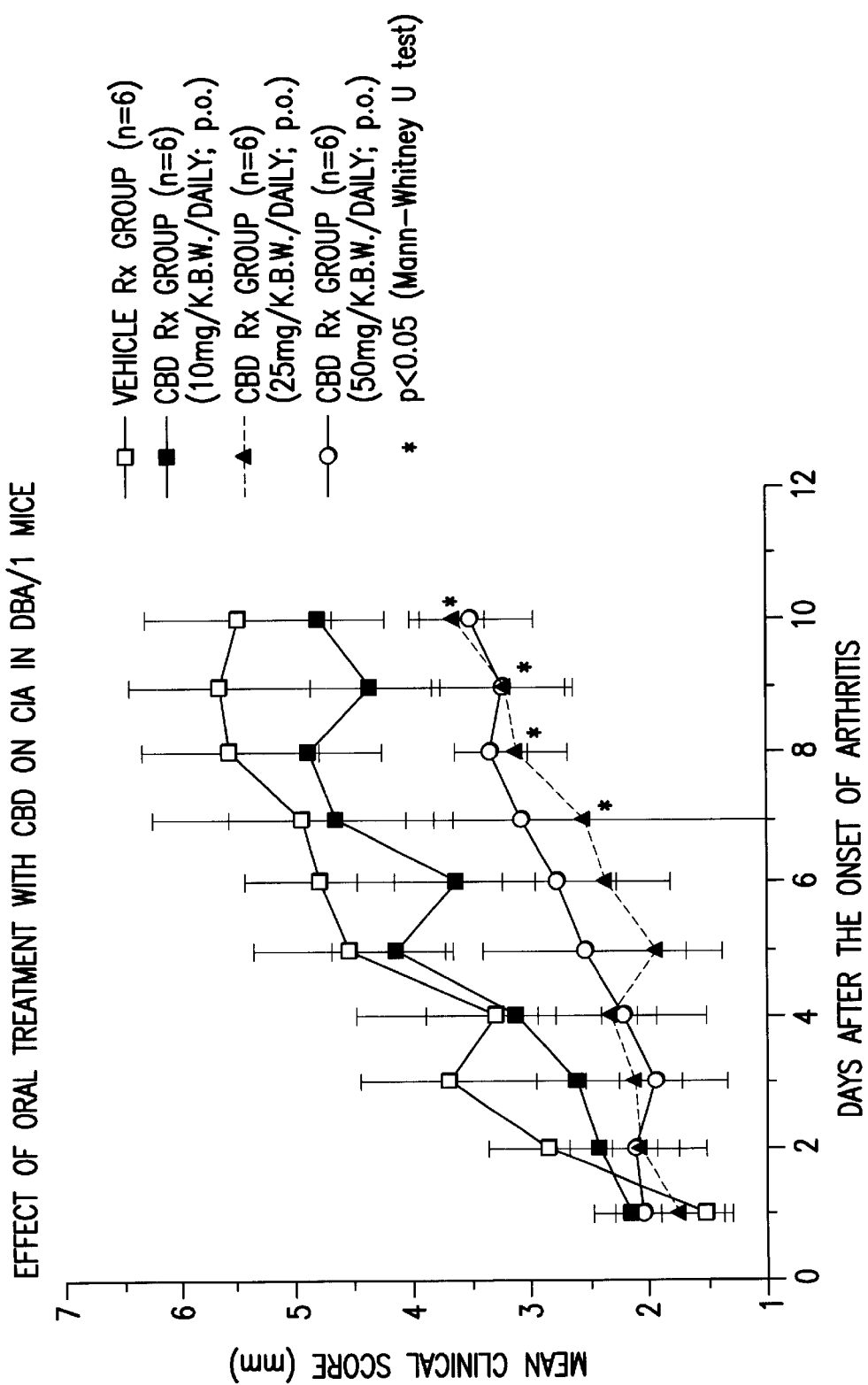
FIG. 5 shows the effect of oral feeding of CBD. From the first signs of arthritis mice were treated daily over a 10 day period with CBD at the concentrations mentioned. The drug was administered by oral gavage. Control mice were fed vehicle (olive oil) along, as described in Materials and Methods. Results are expressed as a mean+/−SEM. The 25 mg/kg group was significantly better than the control group from day 5 onwards (p=0.0411).

Oral Feeding of CBD has a Similar Therapeutic Effect on Established and Chronic Arthritis Daily oral gavage of CBD after onset of arthritis resulted in an adequate suppression of the arthritis (FIG. 5). Again, 25 mg/kg (which corresponds to 5 mg/kg i.p.) was the optimal dose.

Figure 6:
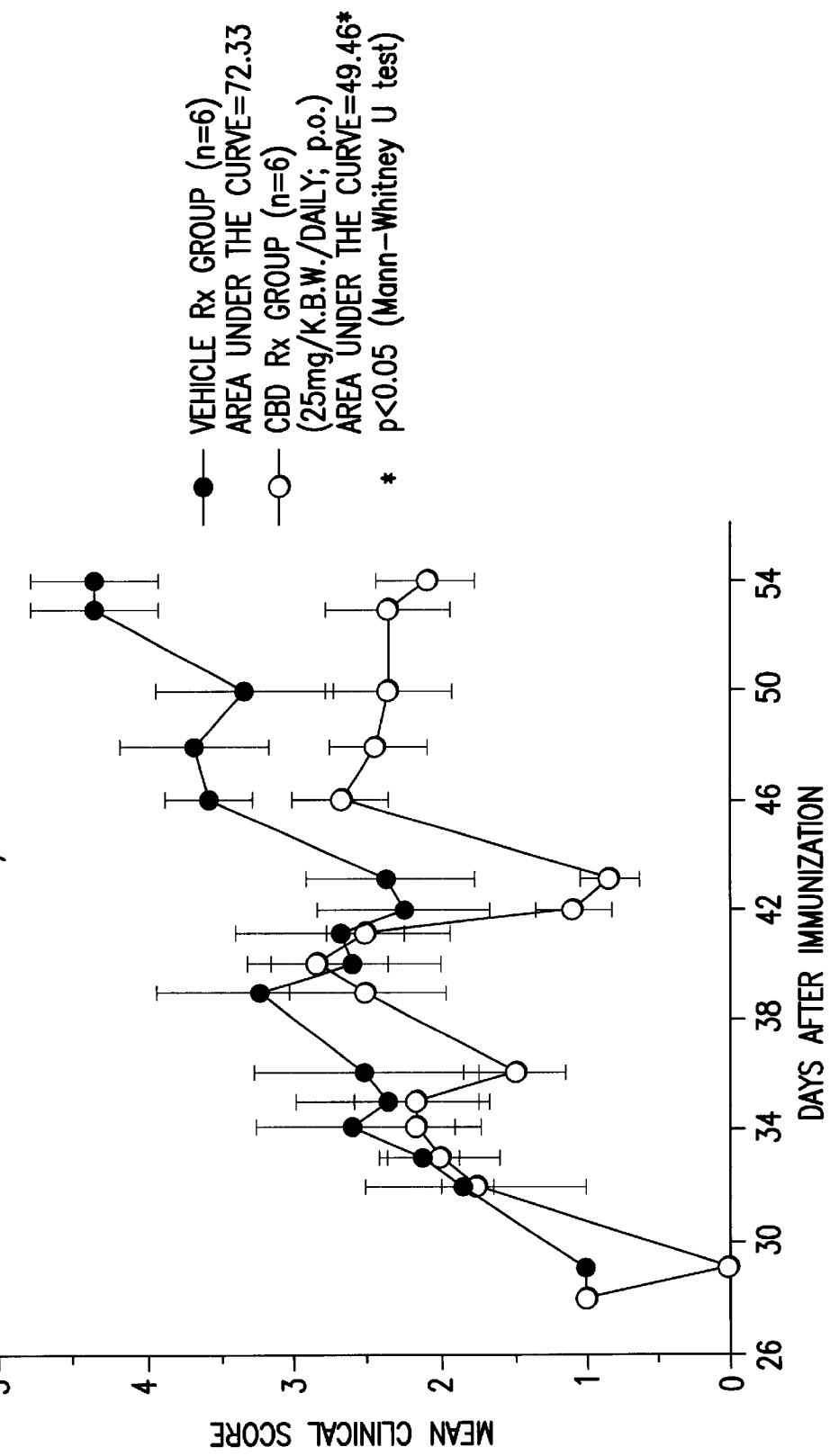
FIG. 6 shows the effect of oral feeding of CBD on chronic CIA. Mice were fed 25 mgfkg CBD. Controls were fed vehicle (olive oil).

FIG. 6 shows that oral feeding of 25 mg/kg CBD resulted in suppression of the progression of chronic CIA. The area under the curve (AVC) was reduced from 72.3 in the controls to 49.7 in the treated animals.

Histological Data Confirm the Clinical Results

Figure 3:
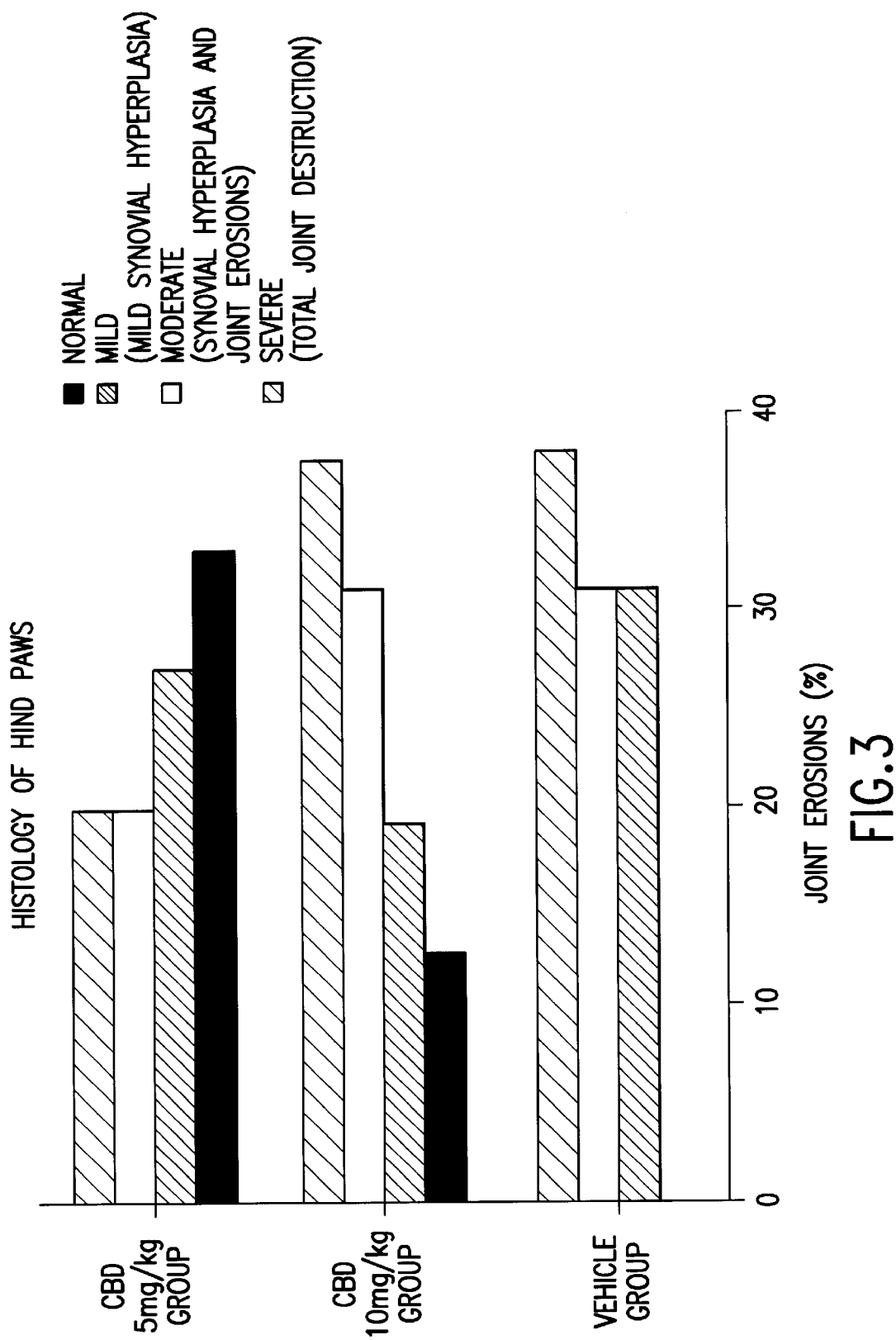
FIG. 3 shows histological data for treating mice with CBD as described in the examples. The hind paws were assessed as normal, mildly affected or severely destroyed.

Joints in the hind paws of control mice and mice treated with CBD, 5 mg/kg and 10 mg/kg, were assessed blindly for hyperplasia and destruction. In the control mice, no normal joints were found whereas 11% of the joints in mice treated with 10 mg/kg CBD and 33% of the joints in mice treated with 5 mg/kg CBD were completely protected (FIG. 3). 69% of all joints in the control mice were moderately or severely affected. In mice treated with 5 mg/kg CBD. this was lowered to 42%. Thus, the histological findings confirm the clinical results that CBD, at 5 mg/kg/day, has a marked therapeutic effect on CIA.

EXAMPLE 5

Cannabidiol Suppression of Autoimmune Encephalomyelitis (EAE) in S3L Mice

The effect of cannabidiol on EAE was studied. EAE resembles the disease state of human multiple sclerosis (MS) and acute disseminating encephalomyelitis.

The methods used were based upon those used by Lehmann D et al. J. Neuroimmunology, Vol. 50, pages 35–42, 1994.

Animals

6–12-week-old female SJL/J mice were purchased from the Jackson Laboratory (Bar Harbor, Me.) and housed under standard conditions in top filtered cages. All animals were fed a regular diet and given acidified water without antibiotics.

Antigens

Mouse spinal cord homogenate (MSCH) was obtained as follows. Spinal cords from 3–10 month-old mice of various strains were obtained by insufflation, MSCH was prepared by homogenization in PBS (1:1 v/v). The homogenate was lyophilized, reconstituted in PBS to a concentration of 100 mg/ml (dry weight) and stored at −20° C. until used.

Tuberculin purified protein derivative (PPD) was obtained from Statens Serum Institute, Copenhagen, Denmark.

Induction and Clinical Evaluation of EAE

Induction of acute EAE in mice was based on a modification of Bernard's procedure (Bernard et al., 1976). Briefly, equal volumes of MSCH (100 mg/ml in PBS) and CFA enriched with *Mycobacterium tuberculosis* H37Ra (6 mg/ml) (Difco Laboratories, Detroit, Mich.) were emulsified. The emulsion (50–100 µl) was administered s.c. (subcutaneously) into the four footpads of each mouse. Immediately thereafter and 2 days later, mice were injected i.v. (intravenously) with pertussigen. All animals were examined daily for signs of disease. The first clinical indications appeared on day 9–11 post immunization and were scored according to the following six point scale: 0, no abnormality; 1, mild tail weakness; 2, tail paralysis; 3, tail paralysis and hind leg paresis;. 4, hind leg paralysis or mild forelimb weakness; 5, quadriplegia or moribund state; 6, death.

Figure 7:
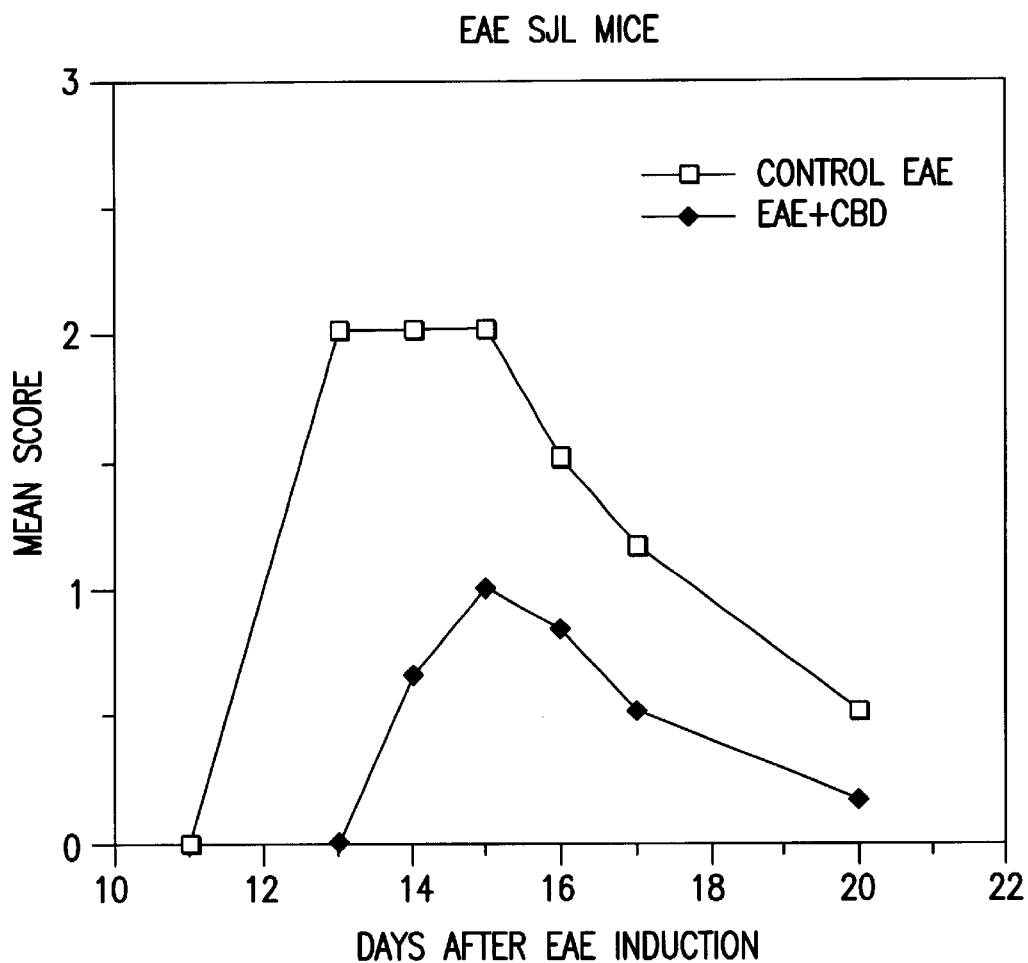
FIG. 7 shows the effects of CBD on experimental autoimmune encephalomylitis. Two groups of 6 SJL/J female mice were injected with mouse spinal cord homogentate to induce EAE. The treatment began at the induction of the disease (day 0) and continued once a day for 14 days. CBD was injected i.p. at a dose of 10 mg/kg. The control group was left untreated.

Mice were treated with cannabidiol at a dose of 10 mg/kg. The results are shown in FIG. 7 and Table 4.

TABLE 4

|  | CONTROL | CBD |
| --- | --- | --- |
| Incidence | 4/6 | 2/6 |
| Duration (days) | 4.66 | 2.16 |
| Mean maximum score | 2 | 1 |

The results show that cannabidiol markedly suppresses EAE in mice.

EXAMPLE 6

The Effect of CBD on Serum TNFα Levels

Figure 8:
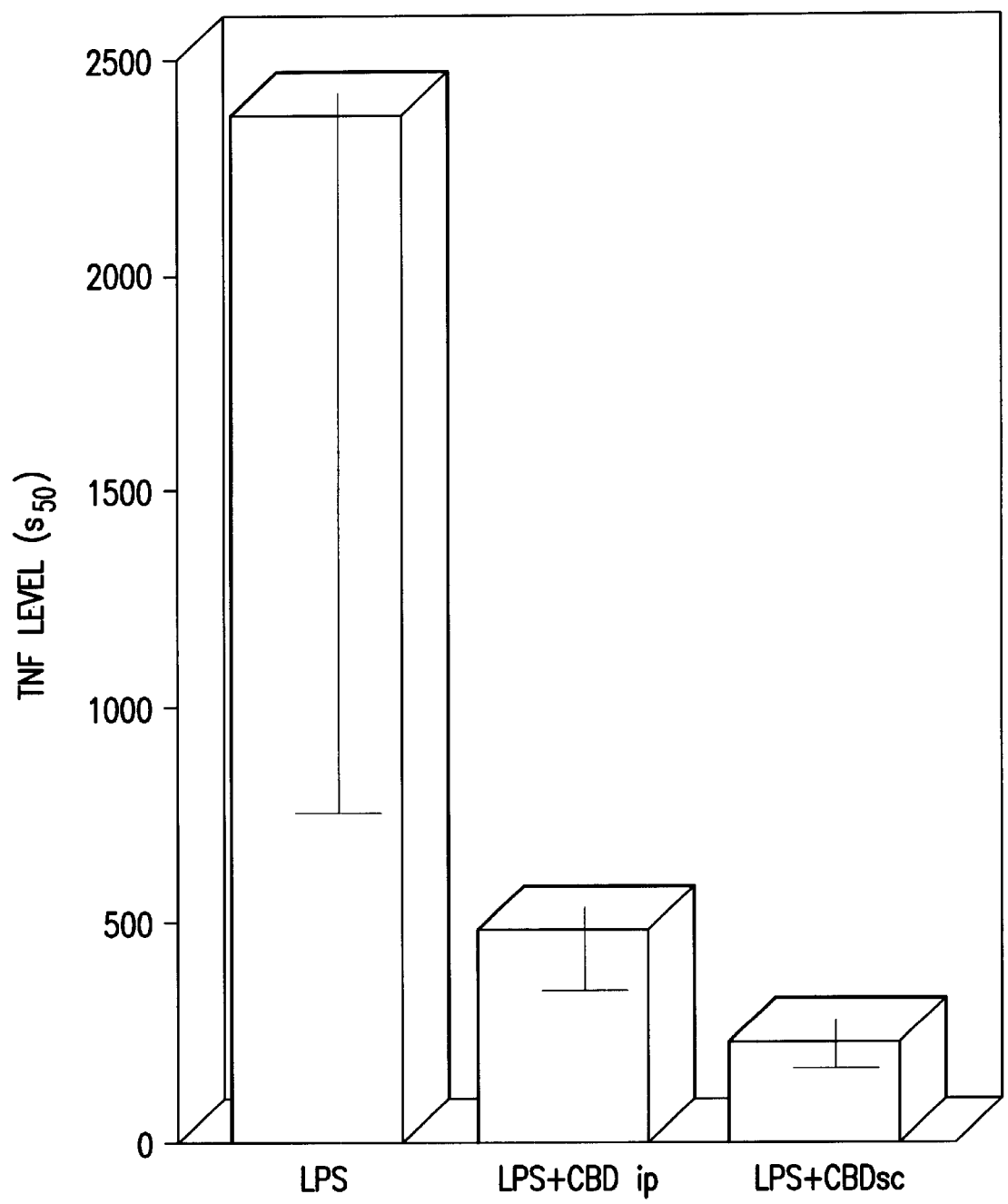
FIG. 8 shows that CBD reduces serum TNFα levels after LPS stimulation. Female C57BL/6 mice were injected ip (intraperitonally) with 100 μg LPS along with CBD ip or subcutaneously (s.c.) 200 μg/mouse (10 mg/kg). After 90 min. the mice were bled and serum TNFα level was determined by bioassay.

FIG. 8 indicates that CBD at 10 mg/kg decreases serum TNFα production in LPS challenged mice.

EXAMPLE 7

The effect of Cannabidiol on T and B Cell Proliferation and Function

Mice and Tumor Cell-lines and Medium

Female mice (aged 8–12 weeks) of strains C57BL/6 (B6, H-$2^b$) and BALB/c (H-$2^d$) were purchased from Harlan, Jerusalem, and maintained under specific pathogen-free (SPF) conditions in the animal facilities of the Hebrew University Medical School, Jerusalem, in accordance with the Hebrew University guidelines, DMEM (Biological Industries, Beit Haemek. Israel) was supplemented with 1 mM sodium pyruvate, 10 mM HEPES buffer, 0.5 mM asparagine-HCl, 0.03 mM filic acid, 0.5 mM L-aspartic acid, $5 \times 10^{-5}$ M 2-mercaptoethanol, 2 mM glutamine, antibotics and 10% FCS (complete DMEM).

Mitogen-induced Cell Proliferation

Spleen cells, at a final concentration of $5 \times 10^6$ cells/ml, were cultured in triplicate wells of flat-bottom microtiter plates (Nunc, Denmark) in medium alone, 2.5 µg/ml concanavalin A (ConA. Biomakor, Israel) or 50 µ/ml lipopolysaccharide (LPS, Difco). The final volume was 200 µl/well. Following two days of incubation at 37° C., in an 8% $CO_2$-in-air incubator (as in all other procedures described here), 1 µCi of $^3$H-thymidine was added to each well. Cells were harvested 6 h later, with a Tomtec (USA) cell harvester and counted in a MicroBeta scintillation counter (Wallac, Finland).

Mixed Leukocyte Reaction (MLR)

Spleen cells ($1 \times 10^6$/well) were co-cultured in triplicate wells of flat-bottom microtiter plates (Nunc), with an equal number of irradiated (25 cGy) syngeneic or allogeneic splenocytes in a final volume of 200 µl/well. After 3-days incubation, the cells were labelled with $^3$H-thymidine (1 µCi/well) and harvested, following an additional incubation of 18 h, as described above.

Mixed Leukocyte Culture (MLC)

MHC-restricted CTL were activated in MLC by co-culturing $2.5 \times 10^6$ responding spleen cells for 5 days with an equal number of irradiated (25 Gy) allogeneic splenocytes in 2 ml/well of complete DMEM in 24-well plates (Costar).

Cell Mediated Cytotoxicity

Cytotoxic assays were performed as described previously (Leshem et al, 1999). Briefly, effector cells were serially diluted (threefold) in triplicate wells of conical-bottom microplates (Nunc) and mixed with washed $^{51}$Cr-labeled target cells in a final 200 µl volume to make 4–6 effector target cell ratios. Microplates were centrifuged (70×g, 2 min.) and incubated for 4 h. They were then centrifuged at 200×g for 5 min. and the supernatants (150 µl) were counted in an automatic c-counter (LKB-Wallac, Finland). Percent of specific cytotoxic activity was calculated according to the formula: [(experimental cpm−background cpm)/(maximal cpm−background cpm)×100]. Lytic units (LU), were drawn from the cytotoxicity measured at 4–6 E:T cell ratios. One 1 LU is defined as the number of effector cells causing lysis of 30% target cells (Leshem and Brass, 1998).

Figure 9A:
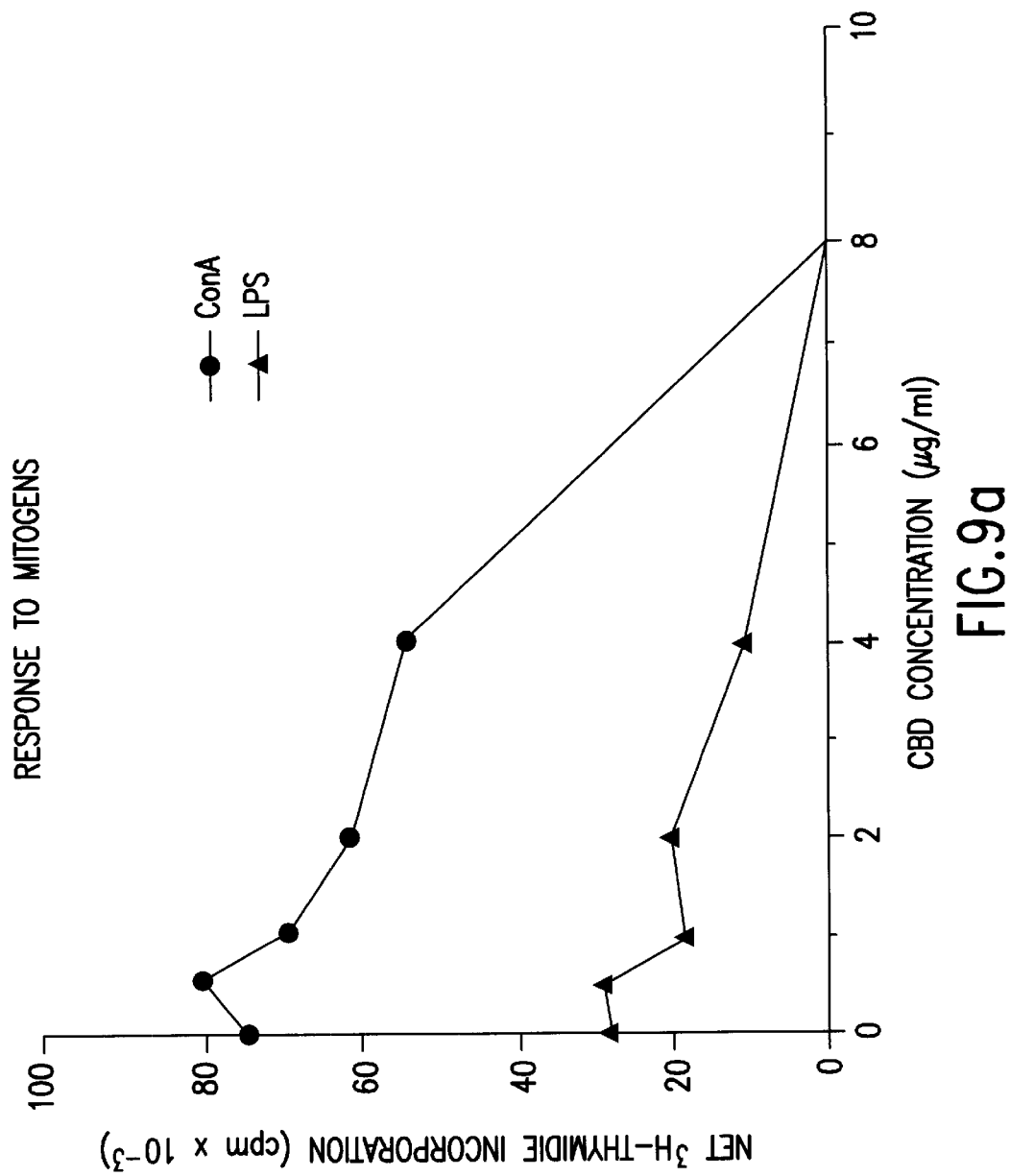
FIG. 9 shows the effect of CBD on response of lymphocytes to Mitogens. Spleen cells ($1 \times 10^6$/well) from either BALB/c (FIG. 9a) or C57BL/b (FIG. 9b) mice were incubated in flat-bottomed microplates for 2 days with medium, 3 μg/ml ConA or 50 μg/ml LPS, in the presence of the indicated concentrations of CBD. Cultures were pulsed with $^3$H-thymidine and harvested 6 hours later.
Figure 9B:
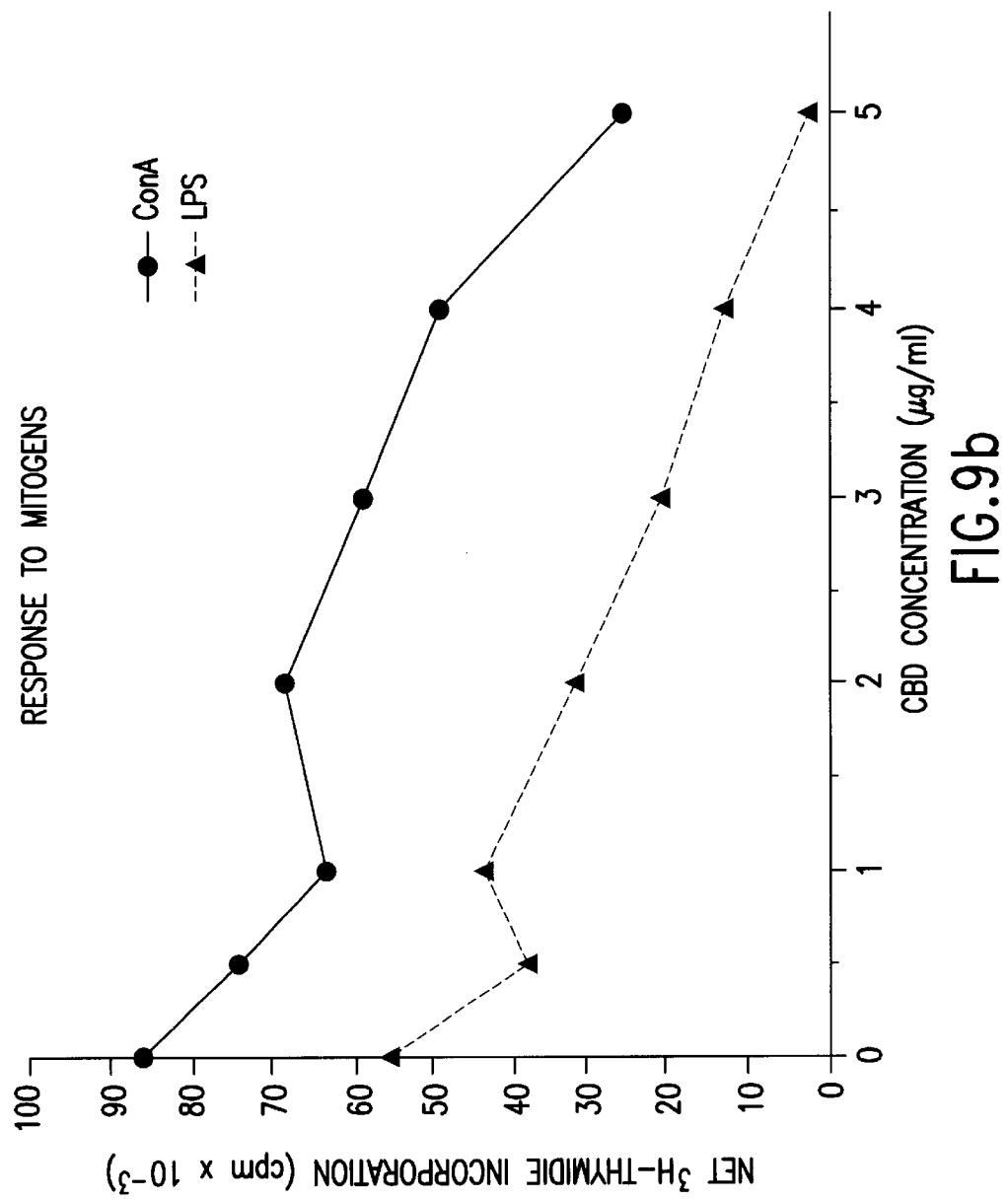

FIGS. 9a and 9b show that CBD decreases the response of BALB/C splenocytes and C57BL/b splenocytes respectively to challenge by Concanavalin A (ConA) and LPS.

Figure 10:
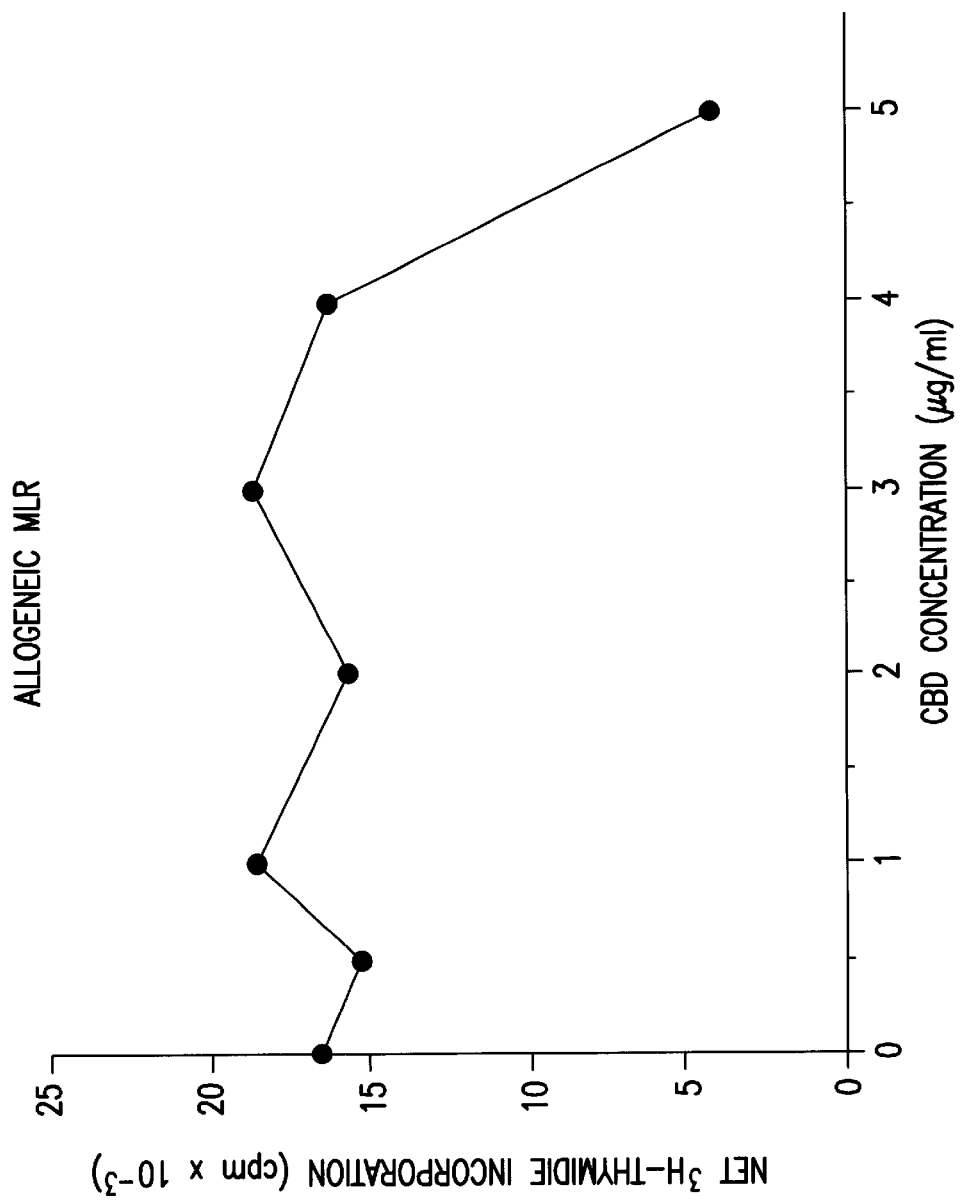
FIG. 10 shows the effect of CBD on mixed leukocyte reaction. Spleen cells ($1 \times 10^6$/well) from either BALB/c mice were incubated in flat-bottomed microplates for 3 days with an equal number of irradiated syngeneic or allogeneic (B6) splenocytes, in the presence of the indicated concentrations of CBD. Cultures were pulsed with $^3$H-thymidine and harvested 18 hours later.
Figure 11:
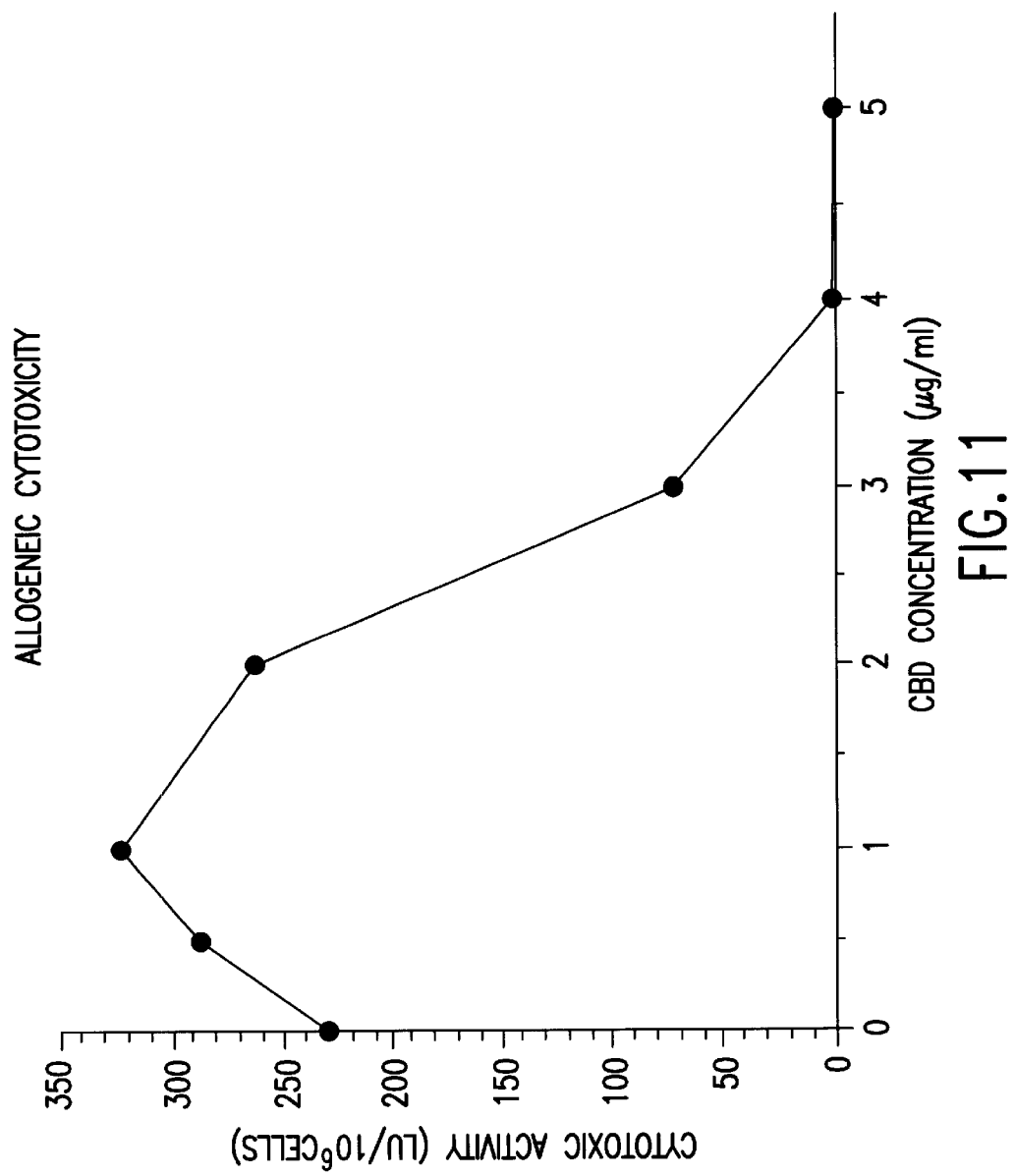
FIG. 11 shows the effect of CBD on cell mediated cytotoxicity. Spleen cells ($1.25 \times 10^6$/ml) from B6 ($H-2^b$) micewere incubated for 5 days with an equal number of irradiated BALB/c ($H-2^d$) splenocytes, in the presence of the indicated concentrations of CBD (mixed leukoyes cultures, MLC). Cells harvested from MLC were tested for their cytotoxic activity against $^{51}$Cr-labeled P815 ($H-2^d$) lymphoma cell line. Cytotoxic activity is given in LU/$10^6$cells (see Materials and Methods).

The effect of CBD on MLR and cell mediated cytotoxicity is shown in FIGS. 10 and 11 respectively. A slight decrease in $^3$H-thymidine uptake was observed above 4 µg/ml CBD. FIG. 11 shows that low concentrations of CBD increase cytotoxicity, above approximately 1 µg/ml CBD though, a decrease in cytotoxicity was observed.

EXAMPLE 8

Reactive Oxygen Intermediation (ROI) Production by Granulocytes is Inhibited by CBD Thioglycollate-elicited granulocytes were harvested from C57BL/6 mice by sterile lavage with PBS 18 hrs. after intraperitoneal injection with 1.5 ml thioglycollate medium (1.5 ml in 3% solution). The cells were washed and resuspended at $5 \times 10^5$ cells/ml in Hanks' buffered salt solution without phenol red, and distributed at 0.5 ml/tube into luminometer plastic tubes. CBD dissolved in ethanol and medium at concentration of 6 μg/ml was added to some tubes and finally luminol 10 μl and zymosan 30 μl was added for 0, 1 or 2 hours. The tube was inserted into luminometer (Biolumate LB 95 oot Berhold Wildbad Germany) which had been prewarmed to 37° C. The granulocyte luminol-enhanced chemiluminescence response to zymosan was considered as the positive control.

All cells were viable at the end of the experiment. CBD inhibited 45–92% of the chemiluminescence peak observed.

TABLE 5

ROI production by Granulocytes from C57BL/6 mice checked by chemiluminescence

| Treatment | Chemiluminescence computer peak | % inhibition |
|---|---|---|
| Granulocytes (control) | 300 | |
| Granulocytes + Zymzan | 1868 | |
| Granulocytes + Zymozan + CBD 6 μg/ml (0 h) | 1024 | 45 |
| Granulocytes + Zymozan + CBD 5 μg/ml (1 h) | 157 | 92 |
| Granulocytes + Zymozan + CBD 6 μg/ml (2 h) | 235 | 87 |

The granulocyte cells were pretreated with CBD 6 μg/ml for 0–2 hours before performing the ROI test. After 1–2 hours of CBD treatment, the cells were about 100% available.

EXAMPLE 9

The Effect of CBD on TNF and Cytokine Release from Rheumatoid Synovial Cells

Culture of Human Rheumatoid Synovial Cells

Synovial membrane tissue was obtained from a patient fulfilling the revised American College of Rheumatology criteria for rheumatoid arthritis who underwent joint replacement surgery. Synovial cell cultures were prepared as described. Briefly, synovial membrane tissue was digested with collagenase type A (1 mg/ml) and DNAase I (0.15 mg/ml) in RPMI 1640 containing 5% FCS for 2 hours at 37° C. The digested tissue was pushed through a 200 μm²-nylon mesh and cultured at $10^6$ cells/ml/well in RPMI 1640 supplemented with 10% FCS, 2mM L-glutamine, and antibiotics in 24-well culture plates at 37° C. in 5% $CO_2$ for 48 hours in complete medium with or without CBD at specified concentrations.

Culture of Murine Synovial Cells

DBA/1 mice which had been immunized with bovine CII in CFA, to induce CIA, as discussed above, were sacrificed at day 10 of arthritis and the knee joints were removed. Synovial cell cultures were performed as previously described. Briefly, synovial membranes were excised under a dissecting microscope and digested with collagenase A (1 mg/ml) (Boehringer-Mannheim) and DNAase type IV (0.15 mg/ml) (Sigma, Dorset, UK) at 37° C. for 20 minutes, in. the presence of polymyxin B (33 μg/ml) (Sigma). The cells were then washed extensively and cultured in 96-well plates at a density of $2 \times 10^6$ cells/ml (100 μ/well) in complete medium with or without CBD at specified concentrations. Supernatants were collected after 24 h. and stored at −20° C. until measured for cytokines.

CBD Suppresses Spontaneous TNF Release by Synovium Taken from Arthritic Animals

Synovial cells from arthritic mice at day 10 are known to spontaneously produce large amounts of TNF when cultured in vitro. It was found that CBD, when added to the in vitro cultures, exerted a dose-dependent suppression of TNF release (Table 6).

The Effect of CBD on Cytokine Release by Human Rheumatoid Synovium

Similarly, rheumatoid synovial cells spontaneously produce cytokines when cultured in vitro. Table 7 shows the effects of CBD on the release of several cytokines, as measured by ELISA. We found a dose-dependent inhibition of IL-6, IL-8, IL-10 and IL-11. In this first initial experiment TNFa was not suppressed which is discordant with the murine results. With restricted number of human synovial cells in this sample, the optimal dose for inhibiting TNFα may have been missed.

TABLE 6

Mouse synovial cells TNFα is inhibited by CBD.

| | O.D. | TNF (pg/ml) |
|---|---|---|
| Synovial cells (SC) | 0.183 ± 0.003 | >1000 |
| SC + vehicle | 0.181 ± 0.004 | >1000 |
| CBD 1 μg/ml | 0.190 ± 0.003 | >1000 |
| CBD 2.5 μg/ml | 0.193 ± 0.004 | >1000 |
| CBD 5 μg/ml | 0.422 ± 0.251 | 100 |
| CBD 10 μg/ml | 0.922 ± 0.103 | 2 |
| CBD 20 μg/ml | 1.152 ± 0.117 | <0.01 |
| CBD 50 μg/ml | 1.163 ± 0.119 | <0.01 |

Well cytotoxicity assay was used.

TABLE 7

Human Rheumatoid Synovial cell cytokine production is regulated by CBD.

| | TNF pg/ml | | IL-6 ng/ml | | IL-8 ng/ml | | IL-10 pg/ml | | IL-11 pg/ml | |
|---|---|---|---|---|---|---|---|---|---|---|
| Drug Dose | mean | sd | mean | sd | mean | sd | mean | sd | mean | sd |
| NIL | 2064 | 184 | 304 | 87 | 175 | 78 | 256 | 54 | 2139 | 70 |
| 20 μg/ml | 2271 | 121 | 125 | 26 | 87 | 34 | 52 | 12 | 100 | 1 |
| 1 μg/ml | 2089 | 783 | 326 | 51 | 183 | 61 | 249 | 30 | 2059 | 216 |
| 0.1 μg/ml | 1963 | 225 | 281 | 43 | 174 | 25 | 273 | 33 | 2151 | 168 |

TABLE 7-continued

Human Rheumatoid Synovial cell cytokine production is regulated by CBD.

| Drug Dose | TNF pg/ml | | IL-6 ng/ml | | IL-8 ng/ml | | IL-10 pg/ml | | IL-11 pg/ml | |
|---|---|---|---|---|---|---|---|---|---|---|
| | mean | sd | mean | sd | mean | sd | mean | sd | mean | sd |
| Control (vehicle) | | | | | | | | | | |
| NIL | 1960 | 94 | 258 | 105 | 165 | 53 | 256 | 24 | 2110 | 78 |
| 20 µg/ml | 1818 | 78 | 322 | 49 | 224 | 79 | 272 | 27 | 1884 | 51 |
| 1 µg/ml | 1656 | 319 | 337 | 70 | 173 | 43 | 223 | 5 | 2110 | 90 |
| 0.1 µg/ml | 1916 | 54 | 310 | 21 | 178 | 48 | 222 | 19 | 1984 | 168 |

What is claimed is:

1. A method of treating a patient suffering from rheumatoid arthritis comprising the step of administering to the patient a pharmaceutically effective amount of cannabidiol.

2. A method of treating a patient suffering from multiple sclerosis comprising the step of administering to the patient a pharmaceutically effective amount of cannabidiol.

3. A method of treating a patient suffering from ulcerative colitis comprising the step of administering to the patient a pharmaceutically effective amount of cannabidiol.

4. A method of treating a patient suffering from Crohn's disease comprising the step of administering to the patient a pharmaceutically effective amount of cannabidiol.

5. The method as in any one of claims 1–4, wherein the cannabidiol is combined with an anti-inflammatory compound.

6. The method as in any one of claims 1–4, wherein the cannabidiol is combined with a pharmaceutically acceptable carrier.

7. The method as in any one of claims 1–4, wherein the effective amount to be administered is between 1 µg/kg/day to 50 mg/kg/day of patient body weight.

* * * * *